(12) United States Patent
Reiffel

(10) Patent No.: US 6,575,889 B1
(45) Date of Patent: Jun. 10, 2003

(54) SCANNING AND FLEXING CHARGED PARTICLE BEAM GUIDE

(76) Inventor: Leonard Reiffel, 602 Deming Pl., Chicago, IL (US) 60614

(*) Notice: Subject to any disclaimer, the term of this patent is extended or adjusted under 35 U.S.C. 154(b) by 0 days.

(21) Appl. No.: 09/937,830

(22) PCT Filed: Nov. 24, 1999

(86) PCT No.: PCT/US99/27991
§ 371 (c)(1),
(2), (4) Date: Sep. 26, 2001

(87) PCT Pub. No.: WO00/61228
PCT Pub. Date: Oct. 19, 2000

Related U.S. Application Data

(60) Provisional application No. 60/128,671, filed on Apr. 9, 1999.

(51) Int. Cl.⁷ .................................................. A61N 5/00
(52) U.S. Cl. ........................................ 600/3; 250/492.3
(58) Field of Search ..................... 600/1–8; 250/492.3, 250/310; 378/65

(56) References Cited

U.S. PATENT DOCUMENTS

| | | | |
|---|---|---|---|
| 5,153,900 A | | 10/1992 | Barkman et al. |
| 5,585,643 A | * | 12/1996 | Johnson ................... 250/492.3 |
| 5,621,780 A | * | 4/1997 | Smith et al. .................. 378/65 |
| 5,816,999 A | * | 10/1998 | Bischoff et al. ............... 600/3 |

* cited by examiner

*Primary Examiner*—John P. Lacyk
(74) *Attorney, Agent, or Firm*—Don Moyer

(57) ABSTRACT

The beam guide (11a) useful in radiation oncology is removably inserted within a body, and scans beams of charged particles into target volumes therein by varying a magnetic field, with magnetic fields serially guiding beams as the guide flexes.

10 Claims, 1 Drawing Sheet

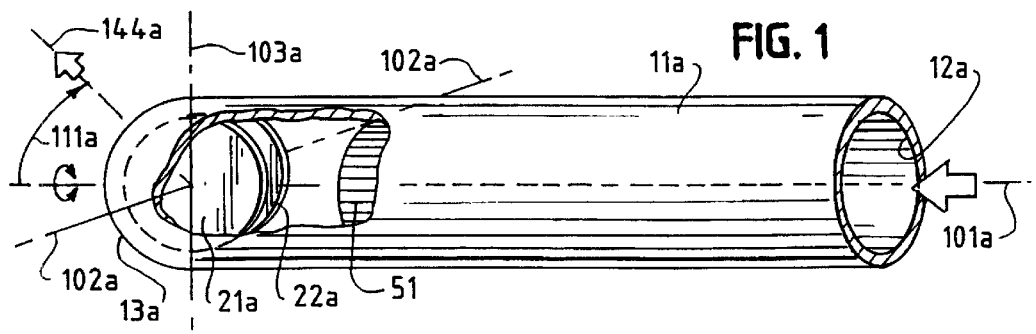
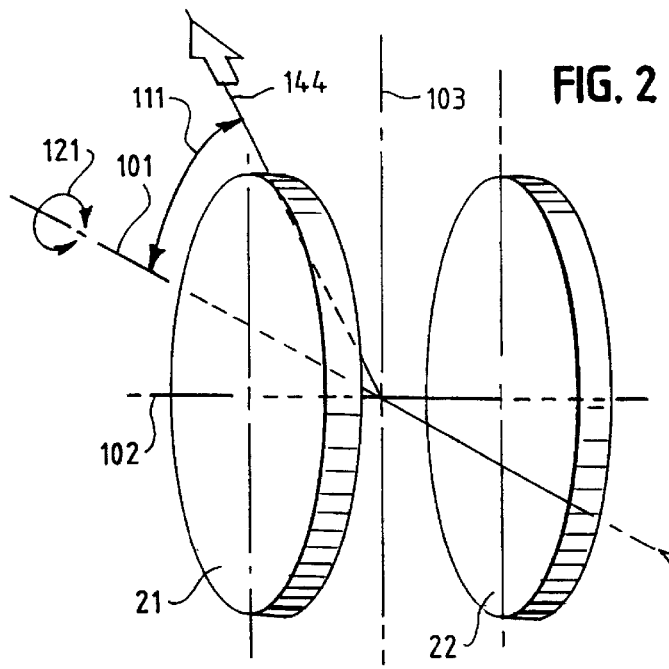
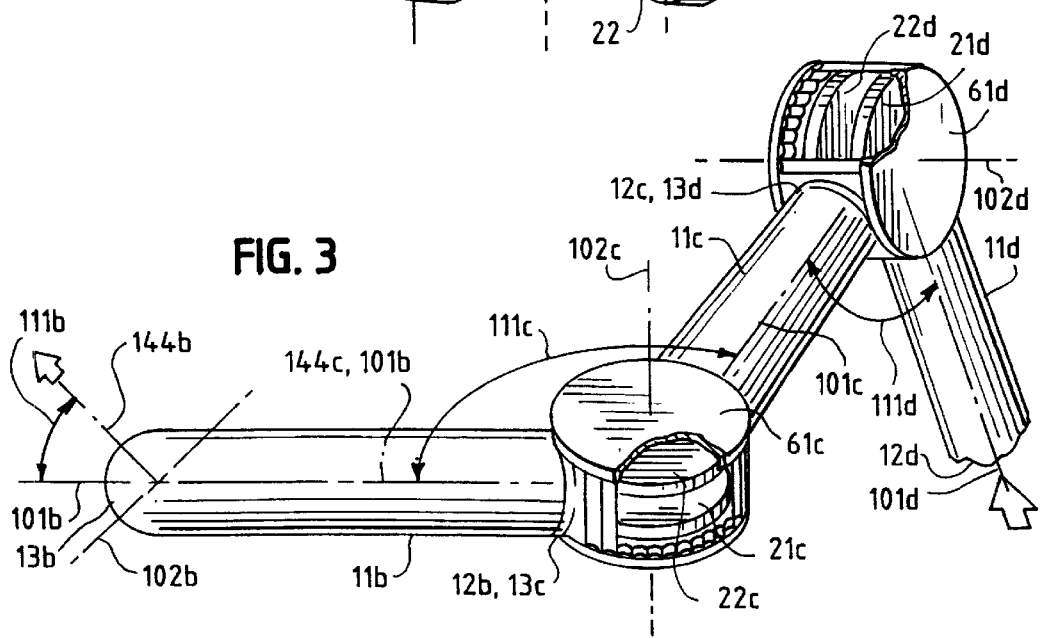

SCANNING AND FLEXING CHARGED PARTICLE BEAM GUIDE

CROSS REFERENCES TO RELATED APPLICATIONS

This application claims benefit of U.S. Provisional Application No. 60/128,671 filed Apr. 9, 1999.

BACKGROUND OF THE INVENTION

This scanning and flexing beam guide is useful in radiation oncology.

When electron beams are used to treat cancerous tumors which are not close to the surface of a body, then there is damage to cells between the surface of the body and the tumor. This long outstanding problem is solved by the discovery shown here of a beam guide which gets an electron beam into the body and scans the beam within the body.

Devices which can be inserted into a body to deliver a radiation dose have been suggested in prior art, for example in U.S. Pat. No. 5,153,900 by Nonikos, U.S. Pat. No. 5,621,780 by Smith, and U.S. Pat. No. 5,585,643 by Johnson. Though Johnson suggests that his device might be made to be flexible, the magnet configuration suggested by Johnson can not produce the flexing, nor the scanning, shown here.

SUMMARY OF THE INVENTION

One form of the beam guide comprises a scanning magnetic field within a sleeve removably inserted in a body, the scanning magnetic field being orthogonal to an entering beam axis, and the scanning magnetic field deflecting the entering beam to form an exiting beam which exits the output end along a scan axis and enters a target volume within the body.

Other forms and objects of the invention will be comprehended in the drawings and detailed description, which will make equivalent forms and objects obvious hereafter to persons skilled in the art.

BRIEF DESCRIPTION OF THE DRAWINGS

FIG. 1 shows a scanning beam guide.

FIG. 2 shows geometrical relations between a beam guide and an exiting beam.

FIG. 3 shows flexing portions in a beam guide.

DESCRIPTION OF THE PREFERRED EMBODIMENTS

The form of the beam guide shown in FIG. 1 has a sleeve 11a which has an input end 12a and an output end 13a. This is also seen in FIG. 3 where the sleeve is 11b, the input end is 12b, and the output end is 13b. An entering charged particle beam enters the input end along a entering beam axis—101 in FIG. 2, 101a in FIG. 1, and 101b in FIG. 3.

There is a magnetic field within the sleeve proximal the output end. The magnetic field is represented by disc magnets—21 and 22 in FIG. 2, 21a and 22a in FIG. 1, and 21c and 22c in FIG. 3. A component of the magnetic field which is orthogonal to the entering beam axis is a scanning magnetic field. This component is parallel to a lateral axis—102 in FIG. 2, 102a in FIG. 1, and 102b in FIG. 3—and orthogonal to a third axis 103.

Charged particles are deflected by the scanning magnetic field so that an exiting beam exits the output end along a scan axis—144 in FIG. 2, 144a in FIG. 2, and 144b in FIG. 3. The scan axis is angled away from the entering axis by a scan angle—111 in FIG. 2, 111a in FIG. 1, and 111b in FIG. 3.

In use, the sleeve is removably inserted into a body, which means that enough of the sleeve is inserted in the body so that the exiting beam exits within the body and enters a target volume within the body from within the body. For example, the sleeve can be sized to be inserted into a person via the anal canal to deliver an electron beam to the prostate. As well, the sleeve can be inserted via purpose made openings such as the openings made for surgery. And, the sleeve can be removably inserted into other organisms via similar openings and into non-animate bodies via similar openings.

The scanning magnetic field can be fixed, can be variable, can keep the beam narrow, and can spread the beam. The scanning magnetic field can be variable by rotation about the entering beam axis as indicated by 121. The scanning magnetic field strength can also be variable to vary the scan angle and thus scan the exiting beam in the plane of the scan angle. The variable scanning magnetic field strength can also vary in accord with beam energy changes. This means that the energy of the beam can be increased and decreased causing the exiting beam to deliver a radiation dose deeper and shallower respectively into the body at any scan angle. Thus, the exiting beam can be scanned so that a radiation dose substantially conforms to a target volume within a body.

The rate of scanning can be controlled so that the dose can be delivered within the target volume with a uniform volume distribution and can be delivered within the target volume with a selected volume distribution. At least one beam property sensor can be included proximal the exiting beam, and elsewhere, to measure a beam property—such as charged particle energies, dose rate, and beam profile—and provide a corresponding beam output signal.

The beam guide can be formed from a series of component guides as in FIG. 3. Here a prior entering beam enters a prior input end 12c of a prior sleeve 11c along a prior entering beam axis 101c and is deflected through a prior scan angle, indicated by the supplement 111c, angled from the prior entering beam axis 101c, by a prior scanning magnetic field—indicated by the disc magnets 21c and 22c. The prior scanning magnetic field is parallel to a prior lateral axis 102c, orthogonal to 101c, and proximate a prior output end 13c of the prior sleeve 11c. The exiting beam exiting the prior output end 13c along a prior scan axis 144c is an entering beam entering an input end 12b a sleeve 11b along an entering beam axis 101b. The entering beam is deflected through a scan angle 111b angled from the entering beam axis 102b to form an exiting beam exiting along a scan axis 144b by a scanning magnetic field—indicated by the disc magnets 21b and 22b—proximate an output end 13b of the sleeve 11b and parallel to a lateral axis 102b orthogonal to 101b.

While the prior scan angle—indicated by the supplement 111c—can be fixed, in the preferred form the prior output sleeve 11c and the sleeve 11b are connected by a flexible joint 61c so that the angle between the sleeve 11b and the prior sleeve 11c—which is the supplement 111c of the prior scan angle—can be varied. While the prior lateral axis 102c can be fixed, in the preferred form the sleeve 11b and the joint 61c can have a component of motion which rotates the prior lateral axis about the prior entering beam axis. Position sensors can be included proximal the joint 61c and elsewhere to measure the angle between the entering beam axis and the prior entering beam axis and produce a position output signal which is received by a scanning magnetic field controller which varies the prior scanning magnetic field accordingly.

The connections and relations between the sleeve 11b and the prior sleeve 11c can be repeated. As shown, another entering beam enters another input end 12d of another sleeve 11d and is deflected through another scan angle, indicated by the supplement 111d, angled from another entering beam axis 101d by another scanning magnetic field—indicated by the disc magnets 21d and 22d. This scanning magnetic field is parallel to another lateral axis 102d, orthogonal to 101d, and proximate another output end 13d at another flexible joint 61d which connects to the prior input end 12c. The prior sleeve 11c can have the same motions relative to its predecessor 11d as the sleeve 11b has with the prior sleeve 11c. The magnetic fields are shown oriented with adjacent scanning magnetic fields being orthogonal in order to illustrate the possibility that it may be necessary to maintain this orientation in order to minimize interactions between strong, adjacent magnetic fields.

In use, at least one of the component guides of the beam guide shown in FIG. 3 is removably inserted in a body in the same way the form shown in FIG. 3b is inserted. "Removably" here in all cases means that the beam guide—in the one component and multiple component forms—is removed intact.

The beam can traverse the sleeve in a vacuum within the sleeve, in a fluid which minimizes radiation loss, and in ordinary air. The sleeve, and the joints, can include materials which will absorb bremsstrahlung radiation. Any of the various methods and devices known in the art for working with charged particle beams can also be included. To indicate this a portion of a collimator 51 is shown.

Though the scanning magnetic field is indicated by a pair of disc magnets, the magnets need not have the disc shape shown; and, a single magnet, two magnets, and more than two magnets, in various orientations, can be used so long as a component orthogonal to the beam—which is the scanning magnetic field—is produced. A magnetic field produced outside the body could supply the scanning magnetic field.

The scanning magnetic field can be supplied by permanent magnets and the scanning magnetic field can be varied by moving magnets closer to and farther from the entering beam axis, can be varied by use of shunts, and can be varied by varying the beam. Ordinary electromagnets can also supply the scanning magnetic field and the field can be varied by varying the current energizing the electromagnet.

The scanning magnetic field can be supplied by a pulsed electromagnet. Magnet pulses and beam pulses can be pulse synchronized to have beam pulses traverse the scanning magnetic field when the scanning magnetic field is at an optimum value.

The scanning magnetic field can also be supplied by superconductive magnets, including high temperature superconductive magnets. When superconductive magnets are used within the sleeve, cooling means known in the art will also be within the sleeve.

The scanning magnetic field can be fixed relative to the entering beam axis and the sleeve can be rotated about the entering beam axis. Also, the scanning magnetic field can be rotated about the entering beam axis. Various mechanical electric, and electro-mechanical methods and devices can also be used for these rotations.

There are several ways to control the scanning magnetic field to keep the scan angle at a desired value. For example, in a case where the magnets 21c and 22c in FIG. 3 are permanent magnets, magnet 21c could be rotated with the sleeve 11b and magnet 22c rotated with the prior sleeve 11c, and the distance between the magnets changed automatically by cams between the magnets. Various mechanical, fluidic, electromechanical, and other actuators known in the art can be use to move magnets—permanent or electrically energized—within the sleeve to vary the scanning magnetic field.

Various mechanical fluidic, electromechanical, and other sensors known in the art can be used measure positions of the magnets, measure positions of a sleeve relative to a prior sleeve and measure properties of the beam and provide input signals to various magnet control devices known in the art which can generate output signals to vary the scanning magnetic field, control actuators, and control devices affecting the beam. If misalignment is detected by at least one sensor, then the charged particle beam can be stopped by various means known in the art.

Using the connections shown in FIG. 3, multiple short component guides can be connected by joints which need only bend through small angles, all of which can be contained in thin flexible covers similar those used for endoscopes. Imaging devices—such as fiber optic imaging devices, acoustic imaging devices, transponders, CT scans, MRI scans, and other imagers known in the art—can be used alone, and in combination, with any form of this beam guide. Acoustic images can be merely echoes from known, natural and implanted, guide points in the body. Imaging devices need only be operationally connected with the beam guide, and can be located inside and outside the body.

In some applications a tube may have been pre-inserted in a body—for example to keep a purpose made channel open. In this case the beam guide can be inserted in the body via the pre-inserted tube.

Components of the beam guide can be adapted scan electrons and other charged particles. The charged particle beam could be produced in a sleeve. While the beam guide is especially useful in radiation oncology, it can also be used in other applications.

Other equivalent forms for a sleeve, a joint between a sleeve and a prior sleeve, imaging devices, and other equivalent ways to provide and vary a scanning magnetic field and to coordinate a scanning magnetic field with motions of a sleeve relative to a prior sleeve will be obvious hereafter to persons skilled in the art. Therefore this invention is not limited to the particular examples shown and described here.

I claim:

1. A charged particle beam guide comprising:
   a sleeve, the sleeve being removably inserted into a body;
   an output end of the sleeve;
   an input end of the sleeve;
   an entering beam axis along which an entering beam of charged particles enters the input end; and
   a scanning magnetic field, the scanning magnetic field being within the sleeve proximal the output end, the scanning magnetic field being orthogonal to the entering beam axis, and the scanning magnetic field deflecting the entering beam to form an exiting beam which exits the output end along a scan axis and enters a target volume within the body, the scan axis being angled from the entering beam axis by a scan angle.

2. The device of claim 1 wherein the scanning magnetic field strength is variable.

3. The device of claim 1 wherein the scanning magnetic field is variable by rotation.

4. The device of claim 2 wherein the scanning magnetic field is variable by rotation.

5. The device of claim 1 further comprising an imaging device operationally connected to the sleeve.

6. The device of claim 1 further comprising:
- a prior sleeve, the prior sleeve being connected to the sleeve at a joint;
- a prior output end of the prior sleeve located at the joint;
- a prior input end of the prior sleeve;
- a prior entering beam axis along which a prior entering beam of charged particles enters the prior input end; and
- a prior scanning magnetic field, the prior scanning magnetic field being within the prior sleeve proximal the prior output end, the prior scanning magnetic field being orthogonal to the prior entering beam axis, and the prior scanning magnetic field deflecting the prior entering beam to form the entering beam which exits the prior output end along the entering beam axis, the entering beam axis being angled from the prior entering beam axis by a prior scan angle.

7. The device of claim 6 further comprising:
- a position sensor located to measure the prior scan angle and provide a position output signal; and
- a scanning magnetic field controller which receives the position output signal and varies the prior scanning magnetic field.

8. The device of claim 1 further comprising a beam property sensor located to measure a beam property and provide a beam output signal.

9. The device of claim 1 wherein the sleeve is inserted into the body via a tube which is pre-inserted in the body.

10. A charged particle beam guide comprising:
- a sleeve, the sleeve being removably inserted into a body;
- an output end of the sleeve;
- an input end of the sleeve;
- an entering beam axis along which an entering beam of charged particles enters the input end;
- a scanning magnetic field, the scanning magnetic field being within the sleeve proximal the output end, the scanning magnetic field being orthogonal to the entering beam axis, the scanning magnetic field deflecting the entering beam to form an exiting beam which exits the output end along a scan axis and enters a target volume within the body, the scan axis being angled from the entering beam axis by a scan angle, the scanning magnetic field strength being variable, and the scanning magnetic field being variable by rotation;
- a prior sleeve, the prior sleeve being rotatably connected to the sleeve at a joint;
- a prior output end of the prior sleeve located at the joint;
- a prior input end of the prior sleeve;
- a prior entering beam axis along which a prior entering beam of charged particles enters the prior input end;
- a prior scanning magnetic field, the prior scanning magnetic field being within the prior sleeve proximal the prior output end, the prior scanning magnetic field being orthogonal to the prior entering beam axis, and the prior scanning magnetic field deflecting the prior entering beam to form the entering beam which exits the prior output end along the entering beam axis, the entering beam axis being angled from the prior entering beam axis by a prior scan angle, prior scanning magnetic field strength being variable, the prior scanning magnetic field being variable by rotation;
- a position sensor located to measure the prior scan angle and provide a position output signal;
- a scanning magnetic field controller which receives the position output signal and varies the prior scanning magnetic field; and
- a beam property energy sensor located to measure a beam property and provide an beam output signal.

* * * * *